United States Patent [19]
Kazmaier et al.

[11] Patent Number: 5,139,909
[45] Date of Patent: Aug. 18, 1992

[54] PERINONE PHOTOCONDUCTIVE IMAGING MEMBERS

[75] Inventors: Peter M. Kazmaier; Ah-Mee Hor; Cheng K. Hsiao, all of Mississauga, Canada

[73] Assignee: Xerox Corporation, Stamford, Conn.

[21] Appl. No.: 560,931

[22] Filed: Jul. 31, 1990

[51] Int. Cl.$^5$ .................................................. G03G 5/47
[52] U.S. Cl. .......................................... 430/59; 430/58; 430/77; 430/78
[58] Field of Search ..................... 430/59, 78, 77, 58

[56] References Cited

U.S. PATENT DOCUMENTS

| | | |
|---|---|---|
| 3,533,785 | 10/1970 | Fox et al. .................. 96/1.5 |
| 3,877,935 | 4/1975 | Regensburger et al. ..... 96/1.5 |
| 3,879,200 | 4/1975 | Regensburger et al. ..... 96/1.5 |
| 3,992,205 | 11/1976 | Wiedemann ................ 96/1.6 |
| 4,396,696 | 8/1983 | Nagasaka et al. .......... 430/78 |
| 4,419,427 | 12/1983 | Graser et al. ............. 430/58 |
| 4,469,769 | 9/1984 | Nakazawa et al. ......... 430/78 |
| 4,587,189 | 5/1986 | Hor et al. ................ 430/59 |
| 4,714,666 | 12/1987 | Wiedemann ............... 430/59 |
| 4,725,520 | 2/1988 | Wiedmann ................ 96/1.6 |
| 4,792,508 | 12/1988 | Kazmiser et al. ......... 430/59 |
| 4,808,506 | 2/1989 | Loutfy et al. ............ 430/59 |

FOREIGN PATENT DOCUMENTS 63-180955  7/1988  Japan ........................ 430/78

Primary Examiner—Marion E. McCamish
Assistant Examiner—Rosemary Ashton
Attorney, Agent, or Firm—E. O. Palazzo

[57] ABSTRACT

A photoconductive imaging member comprised of an unsymmetrical perinone and a charge transport layer.

4 Claims, 2 Drawing Sheets

PERINONE PHOTOCONDUCTIVE IMAGING MEMBERS

BACKGROUND OF THE INVENTION

This invention is generally directed to layered photoresponsive imaging members, and more specifically to photoconductive members comprised of perinone compounds and processes for the preparation thereof. In one embodiment of the present invention, there are provided organic photoconductive layered imaging members comprised of unsymmetrical perinones and charge or hole transport layers comprised of for example, aryl amines as illustrated in U.S. Pat. Nos. 4,265,990 and 4,925,760, the disclosures of which are totally incorporated herein by reference. Further, in one embodiment of the present invention there is provided a photoresponsive imaging member or device with panchromatic visible sensitivity comprised of unsymmetrical perinones of the formulas illustrated herein and the derivatives thereof, and an aryl amine hole transport layer. The photoresponsive imaging members of the present invention can be selected for various electrophotographic imaging and printing processes, especially xerographic processes wherein, for example, latent images are formed thereon followed by development and transfer to a suitable substrate.

Imaging members with symmetrical perinones are illustrated in U.S. Pat. No. 4,808,506, the disclosure of which is totally incorporated herein by reference.

In a patentability search report, there were listed as prior art the following U.S. patents: U.S. Pat. No. 3,879,200 relating to a xerographic plate with photoinjecting bis-benzimidazole pigments as illustrated in, for example, columns 3 and 4; U.S. Pat. No. 3,992,205 which discloses an electrophotographic recording material with a photoconductive multilayer system, see the Abstract of the Disclosure for example, and note formulas (1) to (9), and particularly formula 6 and column 8; U.S. Pat. No. 4,714,666 which discloses perylene tetracarboxylic acid amine pigments for electrophotographic recording systems, see for example the Abstract of the Disclosure; U.S. Pat. No. 4,725,520 directed to, for example, electrophotographic recording materials with certain benzo-benzimidazoquinoline derivatives of the formulas as illustrated in the Abstract of the Disclosure; U.S. Pat. No. 4,792,508, the disclosure of which is totally incorporated herein by reference, which discloses photoconductive layered imaging members with aryl diamine hole transports, see column 9, and as a photogenerating pigment cis, trans perylene isomers of the formula as illustrated in the Abstract of the Disclosure and in column 5; and as secondary interest U.S. Pat. Nos. 3,533,785; 3,877,935; 4,396,696; 4,419,427 and 4,469,769.

Illustrated in U.S. Pat. No. 4,315,981 are double layered electrophotographic recording materials with an electroconductive support and a photoconductive double layer of organic materials with a homogeneous opaque charge carrier producing dyestuff layer obtained from an annealed quinone, or the substitution product thereof selected from the group consisting of dibenzopyrene, quinone, anthraquinone, pyranthrone, dibenzanthrone, and flavanthrone, and a transparent top layer of an insulating material of at least one charge transporting compound. The transport layer contains a charge transporting monomer as reference, for example, in column 2, lines 37 to 56. Further, as indicated in column 4, lines 1 to 22, as the formula 9 compound for the imaging member of the '981 patent there can be selected dibromo-8,16-pyranthrenedione (Indanthrene Orange RRTS, C.I. 59,705). Moreover, it is indicated in column 4, beginning at around line 53, that the organic dyestuff layer may be applied by vapor depositing the dyestuff in a vacuum. Also, this patent discloses a number of resinous binders for the charge transport layer including polycarbonate resins, reference column 7. Further, in U.S. Pat. No. 3,871,882 there are disclosed layered electrophotographic recording materials containing an electroconductive support material and a photoconductive double layer of organic materials, reference for example the Abstract of the Disclosure. Other representative patents of background interest include U.S. Pat. Nos. 3,871,882 and 3,973,959.

In Konishiroku Kokai Japanese 59/184349/A2[84/184349], Oct. 19, 1984, there is disclosed the use of selected pyranthrones as charge generator layers in conjunction with hydrazone charge transport layers. Specifically, a solution coated dispersion of dibromo-8,16-pyranthrenedione in a polymer binder can be selected as the charge generator layer. Also, in U.S. Pat. No. 3,877,935 there are disclosed imaging members with dibromo-8,16-pyranthrenedione vacuum coated charge generator layers contiguous with poly(vinyl carbazole) charge transport layers.

Other prior art that may be of interest includes U.S. Pat. Nos. 4,028,102; 4,399,207; 4,454,211; 4,554,231 and 4,714,666. In the '102 patent, there are illustrated diamine condensation products in double layered photoconductive recording elements. More specifically, there are disclosed in the '102 patent condensation products of o-phenylamine diamine or 1,8-diaminonaphthalene and 4,10-benzothioxanthrene-3,1'-dicarboxylic anhydride of the formulas as illustrated in column 2, and of the formulas 1 to 5, reference column 3, beginning at line 55. The '207 patent discloses electrophotographic photosensitive members with hydrazone compounds of the formula, for example, as illustrated in the Abstract of the Disclosure and in column 2. Examples of charge generating layer materials are illustrated beginning in column 16, line 65, and include, for example, phthalocyanine pigments, perylene pigments, and the like, typical examples of which are specifically recited in columns 17 through 26. The '211 patent discloses electrophotographic photosensitive members with pyrazoline charge transport materials, see for example column 2, beginning at line 35. Specific organic photoconductive materials or charge transporting materials disclosed in the '211 patent are illustrated in columns 3 and 4, formulas 1 and 2, thereof. Charge generating layers for the photoconductive members in the '211 patent are illustrated in column 42, beginning at line 11, and include, for example, organic substances such as pyrylium dyes, thiopyrylium dyes, perylene pigments, and the like with specific examples of charge generating materials being illustrated in columns 42 to 52. Also, it is disclosed in column 57 that a charge generating layer can be formed on an aluminum plate by the vacuum deposition of a perylene pigment having carbon atom bridges at the 1, 12 and 6, 7 positions of the common perylene molecule. In U.S. Pat. No. 4,554,231, there is illustrated an electrophotosensitive member comprised of a layer containing a hydrazone compound of the formula, for example, as illustrated in the Abstract of the Disclosure, which hydrazone compound is selected as charge transport material, reference column 5, line 30, and wherein there are selected various charge generating layer materials including, for example, pyrylium dyes, thiopyrylium dyes, perylene pigments and the like, see column 6, beginning at line 23, and note particularly columns 7 through 12. The use of Vylon 200 on a charge generating layer is disclosed at column 19, lines 15 to 21. In the U.S. Pat. No. 4,714,666 there are illustrated perylene tetracarboxylic acid imide pigments in electrophotographic recording materials, which pigments include those, for example, as represented by the formula 1, reference the Abstract of the Disclosure.

Moreover, in U.S. Pat. No. 4,587,189, the disclosure of which is totally incorporated herein by reference, there are illustrated layered imaging members with photoconductive layers comprised of cis and transbis(-benzimidazo)perylene pigments.

Additionally, numerous different xerographic photoconductive members are known including, for example, a homogeneous layer of a single material such as vitreous selenium, or a composite layered device containing a dispersion of a photoconductive composition. An example of one type of composite xerographic photoconductive member is described, for example, in U.S. Pat. No. 3,121,006 wherein there is disclosed finely divided particles of a photoconductive inorganic compound dispersed in an electrically insulating organic resin binder.

There are also known photoreceptor materials comprised of inorganic or organic materials wherein the charge carrier generating, and charge carrier transport functions are accomplished by discrete contiguous layers. Additionally, layered photoreceptor materials are disclosed in the prior art which include an overcoating layer of an electrically insulating polymeric material. Also, there have been disclosed other layered photoresponsive devices including those comprised of separate generating layers, and transport layers as described in U.S. Pat. No. 4,265,990, the disclosure of which is totally incorporated herein by reference. Examples of photogenerating layers that may be selected include trigonal selenium and phthalocyanines, while examples of transport layers include certain diamines as mentioned herein.

Many other patents are in existence describing photoresponsive devices including layered devices containing generating substances, such as U.S. Pat. No. 3,041,167 which discloses an overcoated imaging member containing a conductive substrate, a photoconductive layer, and an overcoating layer of an electrically insulating polymeric material. This member is utilized in an electrophotographic copying system by, for example, initially charging the member with an electrostatic charge of a first polarity, and imagewise exposing to form an electrostatic latent image, which can be subsequently developed to form a visible image.

Furthermore, there are illustrated in U.S. Pat. No. 4,232,102 and 4,233,383 photoresponsive imaging members comprised of trigonal selenium doped with sodium carbonate, sodium selenite, and trigonal selenium doped with barium carbonate, and barium selenite, or mixtures thereof. Moreover, there is disclosed in U.S. Pat. No. 3,824,099 certain photosensitive hydroxy squaraine compositions. According to the disclosure of this patent, the squaraine compositions are photosensitive in normal electrostatographic imaging systems.

In U.S. Pat. No. 4,508,803, the disclosure of which is totally incorporated herein by reference, there is described an improved photoresponsive device comprised of a supporting substrate, a hole blocking layer, an optional adhesive interface layer, an inorganic photogenerating layer, a photoconducting composition layer comprised of benzyl fluorinated squaraine compositions, and a hole transport layer. Other representative patents disclosing photoconductive devices with squaraine components therein include U.S. Pat. No. 4,507,408; 4,552,822; 4,559,286; 4,507,480; 4,524,220; 4,524,219; 4,524,218; 4,525,592; 4,559,286; 4,415,639; 4,471,041 and 4,486,520. The disclosures of each of the aforementioned patents are totally incorporated herein by reference.

Furthermore, disclosed in the prior art are composite electrophotographic photosensitive materials with various azo compounds. For example, there are illustrated in Japanese Ricoh Patent Publication 6064354, published Apr. 12, 1985, composite photoconductors wherein one of the photoconductor layers contains an azo compound of the formulas as illustrated. Further, there are illustrated in several U.S. patents and publications layered organic electrophotographic photoconductor elements with azo, bisazo, or related compounds. Examples of these patents and publications include U.S. Pat. No. 4,400,455; 4,551,404; 4,390,608; 4,327,168; 4,299,896; 4,314,015; 4,486,522; 4,486,519 and 4,551,404; and Konishiroku Japanese Patent Laid Open Publication 60111247.

Other prior art that may be of background interest includes Japanese Patent 59-59686; Japanese Patent 59-154454; European Patent 100,581; U.S. Pat. No. 4,578,334; European Patent 40,402; U.S. Pat. No. 4,431,721; German Patent 3,110,954; R. O. Loutfy, *Can. J. Chem* 59,544, (1981); and F. Graser and E. Hadicke, *Liebigs Ann. Chem.*, 483 (1984).

Although photoconductive imaging members are known, there remains a need for members with other photogenerator layers. Additionally, there continues to be a need for layered photoresponsive imaging members having incorporated therein perinone compounds, which members will enable the generation of acceptable high quality images and wherein these members can be repeatedly used in a number of imaging cycles without deterioration thereof from the machine environment or surrounding conditions. Moreover, there is a need for improved layered photoresponsive imaging members wherein there is selected as the photogenerator unsymmetrical perinones preferably in contact with specific aryl amine charge transport compositions, which members are sensitive to wavelengths of light of from about 400 to about 700 nanometers. Additionally, there is a need for layered photoconductors with unsymmetrical perinone compounds, which photoconductors are of high sensitivity, that is they posses in an embodiment of the present invention a peak photosensitivity at 550 nanometers of better than 10 ergs/cm$^2$ when calculated with respect to $E_{\frac{1}{2}}$ values (less than 4 ergs/cm$^2$ is preferred), and have low dark decay values of from 0 to about 100 volts, and preferably less than 50 volts/-second, low residual potentials of, for example, less than about 100 volts, and possess high cyclic stability, that is for example stable electricals for more than 20,000 imaging cycles, and are robust. Furthermore, there continues to be a need for photoresponsive imaging members which can be positively or negatively charged thus permitting the development of images, including color images with positively or negatively charged toner compositions. Also, there is a need for disposable imaging members useful in xerographic imaging processes, and xerographic printing systems wherein, for example, light emitting diodes (LED), helium-cadmium or helium-neon lasers, can be selected; and wherein these members are particularly sensitive to the visible region of the spectrum, that is from about 400 to about 700 nanometers. Further, there is a need for processes that will enable the preparation of unsymmetrical perinones with, for example, relatively high volatility and acceptable photosensitivity, which have been heretobefore been inaccessible, it is believed, as attempts to prepare these compounds usually results to the formation of mixtures of symmetrical compounds and the starting anhydride reactant.

SUMMARY OF THE INVENTION

It is therefore a feature of the present invention to provide photoresponsive imaging members with many of the advantages illustrated herein.

A further feature of the present invention is the provision of improved economical photoconductive imaging members comprised of unsymmetrical perinones with high photosensitivity, low dark decay values, and excellent cyclic stability.

Another feature of the present invention resides in the provision of organic layered photoconductive imaging members containing therein certain unsymmetrical perinone compounds as photogenerating layers, and hole transport layers.

In yet another specific feature of the present invention there are provided negatively charged layered photoresponsive imaging members comprised of unsymmetrical perinones optionally dispersed in a resinous binder, and in contact therewith a hole transport layer comprised of aryl amine molecules.

There are provided in another feature of the present invention positively charged layered photoresponsive imaging members with a top photogenerating layer comprised of unsymmetrical perinone photogenerating pigments optionally dispersed in a resinous binder, and thereunder a hole transport layer preferably comprised of aryl amine molecules.

Further, in yet another feature of the present invention there are provided imaging and printing methods with the improved photoresponsive imaging members illustrated herein.

Also, in a further important feature of the present invention there are provided imaging members sensitive to light in the visible region of the spectrum, that is from about 400 to about 700 nanometers.

Another feature of the present invention resides in processes for the preparation of novel unsymmetrical perinones.

In still another feature of the present invention there are provided direct, economical processes for the preparation of unsymmetrical perinones in high yields exceeding, for example, 90 percent in some embodiments.

In another feature of the present invention there are provided processes for the preparation of unsymmetrical perinones of high purity exceeding, for example, 99 percent in some embodiments.

In another feature of the invention there are provided unsymmetrical perinones with, for example, very low dark decay, which perinones are useful as a component in layered imaging members for printers which usually require a lengthy time of from about .5 to about 30 seconds from the time of the initiation of the photoreceptor discharge to the completion of the development. As the resolution of images increases, low speed, high resolution printers will most likely utilize a photoreceptor that tolerates long development times, an advantage achieved with the members of the present invention in an embodiment thereof.

In another feature of this invention there are provided unsymmetrical perinones with long cyclic stability for machine reliability, that is for example a photoreceptor that can be cycled from about 20,000 to 1,000,000 cycles.

These and other features of the present invention can be accomplished by the provision of layered photoconductive imaging members, and more specifically imaging members comprised of perinones. In one embodiment, the layered photoconductive imaging members of the present invention are comprised of photogenerating layers, or layer comprised of unsymmetrical perinone compounds, and in contact therewith a charge or hole transport layer or layers.

In a specific embodiment, the photoconductive layered imaging members of the present invention are comprised of, for example, a supporting substrate, unsymmetrical photogenerating perinone compounds, and an aryl amine hole transport layer.

The unsymmetrical perinones selected for the imaging members of the present invention can be represented by the following formula as illustrated in FIGS. 1A, 1B and 1C wherein R is alkyl with, for example, from 1 to about 26 carbon atoms, such as methyl, ethyl, propyl, butyl, pentyl, hexyl, heptyl, octyl, nonyl, eicosyl, isomers thereof, and the like, aryl with from 6 to about 30 carbon atoms such as naphthyl, anthracenyl, phenyl or substituted phenyl with substituents such as alkyl, halogen, such as chloride, fluoride, bromide, or iodide, cyano substituents; and Ar is an aromatic diamine, such as orthophenylene diamine, a heterocyclic diamine, such as 2,3-diaminopyrazine, pyridine, pyrimidine except 2,3-diaminonaphthalene, or an aliphatic diamine, such as an alkylene diamine, including ethylene diamine.

Specific examples of unsymmetrical perinones selected as the photogenerating component for the imaging members of the present invention include N-phenyl naphthimidazole naphthalene perinone monoimide; N-benzyl naphthimidazole naphthalene perinone monoimide; N-phenethyl naphthimidazole naphthalene perinone monoimide; N-3-chlorophenyl naphthimidazole naphthalene perinone monoimide; N-3-fluorophenyl naphthimidazole naphthalene perinone monoimide; N-2-fluorophenyl naphthimidazole naphthalene perinone monoimide; N-pentafluorophenyl naphthimidazole naphthalene perinone monoimide; cis and trans benzimidazole naphthimidazole perinone; cis and trans 2,3-dichlorobenzimidazole naphthimidazole perinone and 2,3-dimethylbenzimidazole naphthimidazole perinone; and cis and trans imidazole naphthimidazole perinone with from, for example, about 40 to about 60 percent of the cis isomer, and from about 60 to about 40 percent of the trans isomer.

With further respect to the photoconductive imaging members of the present invention, the photogenerating unsymmetrical perinone compounds can be situated between the supporting substrate and the hole transport layer; or alternatively, the hole transport layer may be situated between the supporting substrate and the layer comprised of the unsymmetrical perinone photogenerating compounds. These imaging members may also include protective overcoatings thereover including polymers such as polyurethanes, polycarbonates and the like with a thickness of from about 0.2 micron to about 10 microns, or other effective thicknesses.

In another specific embodiment, the photoconductive imaging member of the present invention is comprised of (1) a supporting substrate; (2) a hole blocking layer; (3) an optional adhesive interface layer; (4) a photogenerating layer comprised of unsymmetrical perinone compounds, and (5) a charge transport layer such as an aryl amine hole transport layer. Thus, the photoconductive imaging member of the present invention in one embodiment is comprised of a conductive supporting substrate, a hole blocking organo silane or siloxane such as described, for example, in U.S. Pat. No. 4,464,450, the disclosure of which is totally incorporated herein by reference, or a metal oxide, such as aluminum oxide, layer in contact therewith, an adhesive layer, such as 49,000 polyester available from Goodyear Chemical, and a photogenerating layer comprised of the unsymmetrical perinone compounds illustrated herein overcoated with certain aryl amines dispersed in a resinous binder.

The unsymmetrical perinone compounds of the present invention can be prepared, for example, by the reaction of a diamino naphthalene, especially 2,3-diamino naphthalene with naphthalene tetracarboxylic acid dianhydride. In one embodiment, the unsymmetrical perinone compounds of the present invention can be prepared by the reaction of diamino naphthalene, especially 2,3-diamino naphthalene with naphthalene tetracarboxylic acid dianhydride in a solvent such as 1-methylpyrrolidinone, which reaction is accomplished in the presence of a catalyst such as a metal halide, including zinc iodide.

In one embodiment, the unsymmetrical perinones of the present invention are prepared by a two step procedure which comprises (1) the reaction of 2,3-diamino naphthalene in 1-methylpyrrolidinone with zinc iodide as catalyst providing after separation by, for example, filtration naphthimidazole naphthalene monoanhydride, the precursor for the unsymmetrical perinones. The second step, reaction of the aforementioned monoanhydride with amines and diamines, can be accomplished in solvents such as acetic acid, 1-chloronaphthalene, 1-methylpyrrolidinone and trichlorobenzene at temperatures of from about 115° to about 250° C. The presence of a lewis acid catalyst, preferably zinc iodide or zinc bromide, accelerates the rate of the reaction.

The 2,3-diamino naphthalene on reaction with naphthalene tetracarboxylic acid provides the monosubstituted product naphthimidazole naphthalene monoanhydride usually in a high (greater than 95 percent in some embodiments) yield as determined by fractional sublimation and infrared comparison with the pure monoanhydride state of purity. This reaction can be accomplished in solvents with a boiling point greater than 160 degrees such as chloronaphthalene, 1-methylpyrrolidine (NMP), 1,2,4-trichlorobenzene and the like with or without the addition of of a lewis acid catalyst, which catalyst can be present in an effective amount of, for example, from about 1 to about 50 mole percent, such as zinc iodide, zinc bromide, zinc chloride, ferric chloride or zinc acetate. More specifically, the reactants, naphthalene tetracarboxylic acid and 2,3-diamino naphthalene, and sufficient solvent to maintain the reaction mixture in an easily stirrable state (a ratio of from about 20 parts to 100 parts of solvent per part of anhydride being typical) are mixed in a reaction vessel. The reactants are stirred and heated to a temperature of from about 120° to about 260° C. for a period of from 1 to about 150 hours which results in the monoaddition of the diamino naphthalene to the anhydride and the elimination of water enabling formation of the naphthimidazole naphthalene monoanhydride. Optionally, a catalyst as ilustrated herein can be used to increase the reaction rate. Zinc compounds such as zinc iodide, zinc acetate and the like, as illustrated herein, in an amount of from about 0.01 mole to 0.5 mole per mole of anhydride are particularly effective as catalysts. The reaction mixture is then filtered while at a temperature of from about 100° to about 140° C. with a sintered glass funnel and the filtered product can be washed with hot solvent, such as dimethyl formamide, tetrahydrofuran, acetone, N-methylpyrrolidone, toluene, water, nitrobenzene and tetralin at a temperature of from about 25° to about 200° C. The washing removes impurities and undesirable side products formed during the reaction. The desired naphthimidazole naphthalene monoanhydride is further washed with a low-boiling solvent such as an alcohol including methanol, tetrahydrofuran or acetone and dried at ambient temperature to constant weight. The above compound can be converted into the bisbenzimidazo and imide naphthimidazo perinones illustrated herein by reaction with aromatic diamines, heterocyclic diamines, or aliphatic diamines including substituted orthophenylenediamine, substituted anilines or alkyl amines in a refluxing solvent such as 1-methylpyrrolidone (NMP) or 1-chloronaphthalene solvent, reference Examples III to XIII. The perinones can then be separated from the reaction mixture by filtration and can be washed as indicated herein. Thereafter, additional purification of the perinone product can be obtained by known sublimination processes. The reaction rate can be increased by the use of catalysts such as zinc iodide and the like. The structures of the unsymmetrical perinone pigments were established by a combination of elemental analyses, high-resolution 1 H nuclear magnetic resonance spectroscopy, UV-VIS-NIR spectroscopy, infrared spectroscopy, elemental analysis, mass spectrometry, and the like as indicated herein.

The unsymmetrical perinones of the present invention can be further purified prior to incorporation in the imaging members by fractional sublimation, which involves subjecting the perinones illustrated herein to a temperature of from about 350° to about 650° C., whereby impurities and decomposition products more volatile than the desired components are separated at a temperature zone of below 200° C. There are thus obtained the desired purified unsymmetrical perinone components at a purity of at least about 98 percent at a temperature zone of from about 290° to about 460° C. separated from the nonvolatile impurities, which remain at the high temperature (500° to 650° C.) zone. The sublimation apparatus used has been described by H. J. Wagner et al. in *Journal of Materials Science*, Vol. 17, pp 2781 to 2791, (1982), the disclosure of which is totally incorporated herein by reference.

Various known processes can be selected for the preparation of the photoconductive imaging members of the present invention, the process parameters and the order of coating of the layers being dependent on the member desired. Specifically, for example, in one method the unsymmetrical perinone photogenerating layer is deposited on a supporting substrate by vacuum sublimation, and subsequently the hole transport layer is deposited thereover by solution coating. In another process variant, the layered photoconductive device can be prepared by providing the conductive substrate containing the hole blocking layer and an optional adhesive layer, and applying thereto by solvent coating processes, laminating processes, or other methods, the unsymmetrical perinone photogenerating layer, and the charge transport layer comprised preferably of an aryl amine. The aforementioned processes are well known and are, for example, illustrated in some of the prior art, especially U.S. patents mentioned herein.

The photoconductive imaging members of the present invention can be incorporated into numerous imaging processes and apparatuses inclusive of those well known in the art such as xerographic imaging and printing processes. Specifically, the imaging members of the present invention are useful in xerographic imaging processes wherein the unsymmetrical perinone pigments absorb light of a wavelength of from about 400 nanometers to about 700 nanometers. In these processes, electrostatic latent images are initially formed on the imaging member, followed by development with a toner, reference for example U.S. Pat. No. 4,560,635, the disclosure of which is totally incorporated herein by reference, thereafter transferring the image to a suitable substrate, and fixing the developed image thereto by, for example, heat, a combination of heat and pressure, and the like.

BRIEF DESCRIPTION OF THE DRAWINGS

For a better understanding of the present invention and further features thereof, reference is made to the following detailed description of various embodiments wherein FIG. 1(A-C) represents perinone compounds of the present invention wherein the substituents are as defined herein, and wherein in FIGS. 1B and 1C the perinones are comprised of a mixture of a cis and trans isomer with from about 40 to about 60 percent by weight of the cis isomer, and from about 60 to about 40 weight percent of the trans isomer.

DESCRIPTION OF SPECIFIC EMBODIMENTS

Specific embodiments of the present invention will now be provided with reference to specific photoconductive imaging members containing the unsymmetrical perinone compounds illustrated herein.

Figure 2:
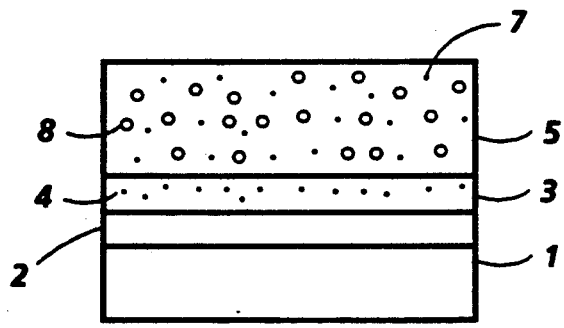
FIG. 2 is a partially schematic cross-sectional view of a photoresponsive imaging member of the present invention in which the perinone photogeneration layer is situated between a substrate and a charge transport layer.

Illustrated in FIG. 2 is a photoresponsive imaging member of the present invention comprised of a substrate 1, an adhesive layer 2, a photogenerator layer 3 comprised of the unsymmetrical perinones illustrated herein, and preferably N-phenyl naphthimidazole naphthalene perinone monoimide, N-benzyl naphthimidazole naphthalene perinone monoimide, N-phenethyl naphthimidazole naphthalene perinone monoimide, N-3-chlorophenyl naphthimidazole naphthalene perinone monoimide, N-3-fluorophenyl naphthimidazole naphthalene perinone monoimide, N-2-fluorophenyl naphthimidazole naphthalene perinone monoimide, N-pentafluorophenyl naphthimidazole naphthalene perinone monoimide, cis and trans benzimidazole naphthimidazole perinone, cis and trans 2,3-dichlorobenzimidazole naphthimidazole perinone and 2,3-dimethylbenzimidazole naphthimidazole perinone, and cis and trans imidazole naphthimidazole perinone, optionally dispersed in a resinous binder composition 4 and a charge carrier hole transport layer 5 comprised of an aryl amine such as N,N'-diphenyl-N,N'-bis(3-methylphenyl)-[1,1'-biphenyl]-4,4'-diamine 7 dispersed in a polycarbonate resinous binder 8.

Figure 1A:
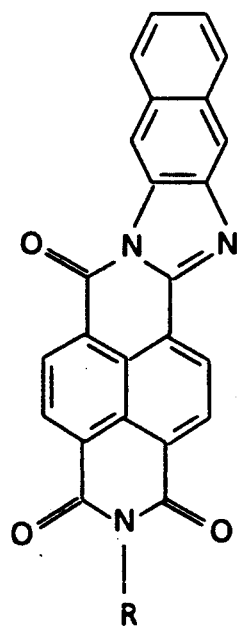
Figure 3:
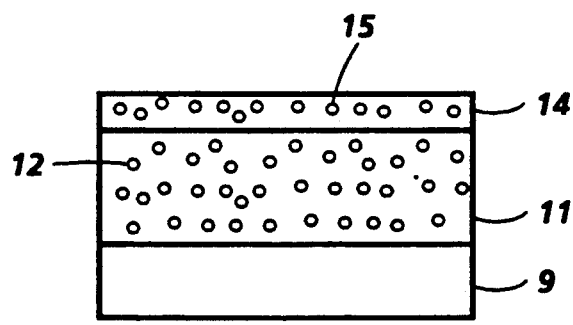
FIG. 3 is a partially schematic cross-sectional view of a photoresponsive imaging member of the present invention in which a charge transport layer is situated between a perinone photogeneration layer and a substrate.

Illustrated in FIG. 3 is a photoresponsive imaging member in which the hole transport layer is situated between the supporting substrate and the photogenerating layer. More specifically, with reference to this Figure, there is illustrated a photoconductive imaging member comprised of a supporting substrate 9, a hole transport layer 11 comprised of the aryl amine hole transport composition dispersed in an inactive resinous binder composition 12, and a photogenerating layer 14 comprised of the unsymmetrical perinones illustrated in FIG. 1 optionally dispersed in a resinous binder composition 15.

Figure 4:
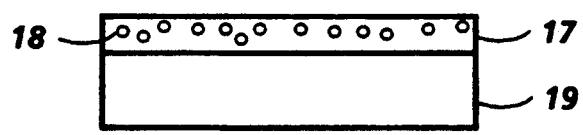
FIG. 4 is a single photoresponsive imaging member of the present invention which is comprised of an unsymmetrical perinone compound which functions as a photogenerating pigment and a hole transport layer.

Illustrated in FIG. 4 is a photoresponsive imaging member comprised of a single layer 17 of the unsymmetrical perinones illustrated herein optionally dispersed in a resinous binder 18, and coated onto a substrate 19. Photogeneration as well as charge transport is accomplished in the single layer 17. The single layer may be comprised of the unsymmetrical perinone pigments with or without charge transport molecules such as aryl amines dispersed in a resinous binder composition.

The supporting substrates may comprise a layer of insulating material such as an inorganic or organic polymeric material, including Mylar a commercially available polymer; a layer of an organic or inorganic material having a semiconductive surface layer such as indium tin oxide or aluminum arranged thereon, or a conductive material such as, for example, aluminum, chrominum, nickel, titanium, brass, or the like. The substrate may be flexible, seamless, or rigid and many have a number of different configurations, such as for example a plate, a cylindrical drum, a scroll, an endless flexible belt, a seamless belt, and the like. Preferably, the substrate is in the form of an endless flexible belt. In some situations, it may be desirable to coat on the back of the substrate, particularly when the substrate is an organic polymeric material, an anticurl layer, such as for example polycarbonate materials commercially available as Makrolon. The thickness of the substrate layer depends on many factors, including economic considerations, thus this layer may be of substantial thickness, for example over 100 mils, or of minimum thickness providing there are no adverse effects on the system. In one preferred embodiment, the thickness of this layer is from about 3 mils to about 10 mils.

The optional adhesive layers are typically comprised of a polymeric material including polyesters, such as those available from E.I. DuPont 49,000, PE-100 polyesters, poly(vinyl butyral), poly(vinyl pyrrolidone), and the like. Typically, this layer is of a thickness of less than about 5 microns and preferentially is of a thickness of from about 0.05 to about 1 micron. The imaging member of the present invention can include other layers as illustrated herein, including metal oxide layers such as aluminum oxide and siloxanes such as gamma aminopropylsilane, reference U.S. Pat. No. 4,464,450, the disclosure of which is totally incorporated herein by reference. Generally, the thickness of these layers is from about 0.05 to about 1 micron, however, other thicknesses may be selected.

The perinone photogenerating layers are generally of an effective thickness of, for example, from about 0.05 micron to about 10 microns, or more, and preferably are of a thickness of from about 0.1 micron to about 3 microns; however, the thickness of this layer is primarily dependent on the photogenerator weight loading which may vary from about 5 to 100 percent. Generally, it is desirable to provide this layer in a thickness which is sufficient to absorb about 90 percent or more of the incident radiation which is directed upon it, and the imagewise or printing exposure step. The maximum thickness of this layer is dependent primarily upon factors such as mechanical considerations, for example whether a flexible photoconductive imaging member is desired, the thicknesses of the other layers, and the specific perinone compound selected. The perinones may be dispered in known resin binders such as polyvinyl carbazole, polycarbonates, and the like.

Various suitable aryl amine charge, especially hole transport, layers can be selected for the photoconductive imaging members of the present invention, which layer has a thickness, for example, of from about 5 microns to about 75 microns, and preferably is of a thickness of from about 10 microns to about 40 microns. In a preferred embodiment, this transport layer comprises aryl amine molecules of the following formula

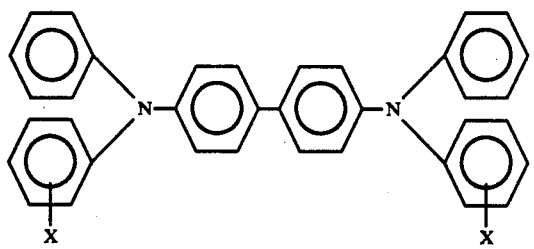

dispersed in a highly insulating and transparent organic resinous binder wherein X is selected from the group consisting of alkyl and halogen, and preferably (ortho) CH$_3$, (meta) CH$_3$, (para) CH$_3$, (ortho) Cl, (meta) Cl, or (para) Cl. Compounds corresponding to the above formula include, for example, N,N'-diphenyl-N,N'-bis(alkylphenyl)-[1,1-biphenyl]-4,4'-diamine wherein the alkyl is selected from the group consisting of methyl such as 2-methyl, 3-methyl, and 4-methyl, ethyl, propyl, butyl, hexyl, and the like. With halo substitution, the amine is N,N'-diphenyl-N,N'-bis(halo phenyl)-[1,1'-biphenyl]-4,4'-diamine, wherein halo is 2-chloro, 3-chloro, or 4-chloro.

Examples of the highly insulating and transparent resinous material or inactive binder resinous material for the photogenerating or transport layers include materials such as those described in U.S. Pat. No. 3,121,006, the disclosure of which is totally incorporated herein by reference. Specific examples of organic resinous materials, especially for the transport layer, include polycarbonates, acrylate polymers, vinyl polymers, cellulose polymers, polyester, polysiloxanes, polyamides, polyurethanes and epoxies as well as block, random or alternating copolymers thereof. Preferred electrically inactive binder materials for the charge transport are polycarbonate resins having a molecular weight ($M_w$) of from about 20,000 to about 100,000 with a molecular weight in the range of from about 50,000 to about 100,000 being particularly preferred. Generally, the resinous binder contains from about 10 to about 75 percent by weight of the charge transport material corresponding to the foregoing formula, and preferably from about 35 percent to about 50 percent of this material. Polyvinyl carbazole is a preferred binder for the photogenerator pigment.

Also included within the scope of the present invention are methods of imaging with the photoconductive imaging members illustrated herein. These methods generally involve the formation of an electrostatic latent image on the imaging member, followed by developing the image with known developer compositions, reference for example U.S. Pat. Nos. 3,590,000; 4,469,770; 4,560,635 and 4,298,672, the disclosures of which are totally incorporated herein by reference; subsequently transferring the image to a suitable substrate; and permanently affixing the image thereto.

The invention will now be described in detail with reference to specific preferred embodiments thereof, it being understood that these examples are intended to be illustrative only. The invention is not intended to be limited to the materials, conditions, or process parameters recited herein. Also, all parts and percentages are by weight unless otherwise indicated.

EXAMPLE I

Preparation of Naphthimidazole Naphtalene Monoanhydride (NPNMA)

A three-necked, round-bottomed reaction flask equipped with mechanical stirrer, reflux condenser and nitrogen inlet tube was charged 2,3-diamino naphthalene (0.324 mole), naphthalene tetracarboxylic acid dianhydride (0.324 mole), zinc iodide (0.015 mole) and 1-methylpyrrolidinone (300 milliliters). The reaction mixture was heated at reflux (200°) for 3.3 hours and the product was isolated by filtration. After washing the product naphthimidazole naphthalene monoanhydride, containing some symmetrical naphthimidazole perinone, twice with hot toluene and drying to constant weight, the yield was 89.7 percent. Analysis of the product by IR and comparing the peak ratios to authentic samples, about 3 milligrams, of naphthimidazole perinone, naphthalene tetracarboxylic acid dianhydride and a sublimed sample of naphthimidazole naphthalene monoanhydride indicated that the product was about 80 percent NPNMA.

Sublimation of the isolated 80 percent NPNMA in a train nitrogen gas under vacuum and isolation of the fractions (the other major component naphthimidazole perinone, the symmetric product, condenses at a higher temperature than NPNMA) confirmed the aforementioned results. The mass spectrum of the pure, about 98 to about 100 percent NPNMA isolated product, showed a molecular ion at M/z 390. Infrared bands occured at 1,775, 1,747 and 1,701 cm$^{-1}$.

EXAMPLE II

Preparation of Naphthimidazole Naphthalene Monoanhydride

A three-necked, round-bottomed reaction flask equipped with mechanical stirrer, reflux condenser and nitrogen inlet tube was charged with naphthalene tetracarboxylic acid dianhydride (0.03 mole), zinc iodide (0.015 mole) and 1-methylpyrrolidinone (300 milliliters). The reaction mixture was heated at reflux (200°) and 2,3-diamino naphthalene (0.03 mole) was added dropwise by syringe pump over 4 hours. After the addition was complete, the product naphthimidazole naphthalene monoanhydride was isolated by filtration. After washing the product twice with hot toluene and drying to constant weight, the yield was 64 percent. Analysis of the product by IR and comparing the peak ratios to authentic samples of naphthimidazole perinone, naphthalene tetracarboxylic acid dianhydride and a sublimed sample of naphthimidazole naphthalene monoanhydride indicated that the product was approximately 95 percent NPNMA. As described in Example I, sublimation and isolation of the fractions confirmed these results. The mass spectrum of the product showed a molecular ion at M/z 390. Infrared bands occured at 1,775, 1,747 and 1,701 cm$^{-1}$.

EXAMPLE III

Preparation of Unsymmetrical Perinone N-Phenyl Naphthimidazole Naphthalene Monoimide Naphthimidazole naphthalene monoanhydride (0.0128 mole) obtained from Example I, aniline (0.064 mole), and zinc iodide (5 mole percent) were reacted in NMP (1-methylpyrrolidinone) at about 203° to about 206° C. for 4 hours. The above resulting product was isolated by filtration, washed with hot toluene and acetone, and dried to constant weight (yield 71 percent). The infrared showed bands at 1,712 and 1,672 cm$^{-1}$ confirming that the starting material naphthimidazole naphthalene monoanhydride had been converted to N-phenyl naphthimidazole naphthalene perinone monoimide.

Combustion analysis: Found: C: 77.02 H: 3.19 N: 9.34; Calculated: C: 77.41 H: 3.25 N: 9.03.

EXAMPLE IV

Preparation of Unsymmetrical Perinone N-Pentafluorophenyl Naphthimidazole Naphthalene Monoimide Naphthimidazole naphthalene monoanhydride (0.114 mole), obtained from Example I, pentafluoroaniline (0.137 mole), and zinc iodide (5 mole percent) were reacted in NMP at 203° to 206° for 76 hours. The product red crystals were isolated by filtration washed with hot toluene and acetone, and dried to constant weight (yield 79.9 percent). The product N-pentafluorophenyl naphthimidazole naphthalene perinone monoimide showed bands in the infrared at 1,726 and 1,696 cm$^{-1}$. Mass spectroscopy showed a molecular ion at M/z 555.

Combustion analysis: Found: C: 64.71 H: 1.91 N: 8.06 F: 16.88; Calculated: C: 64.88 H: 1.82 N: 7.57 F: 17.10.

EXAMPLE V

Preparation of Unsymmetrical Perinone Benzimidazole Naphthimidazole Naphthalene Naphthimidazole naphthalene monoanhydride (0.0128 mole), obtained from Example I, orthophenylene diamine (0.064 mole), and zinc iodide (5 mole percent) were reacted in NMP at 205° for 5 hours. The resulting brown crystals were isolated by filtration washed with hot toluene and acetone, and dried to constant weight (yield 90.2 percent) of the above perinone product. The benzimidazole naphthalene perinone showed a strong infrared band at 1,696 cm$^{-1}$ indicative of the diimidazole structure.

EXAMPLE VI

Preparation of Unsymmetrical Perinone 4,5-Dimethylbenzimidazole Naphthimidazole Naphthalene Naphthimidazole naphthalene monoanhydride (0.0128 mole), obtained from Example I, ortho-4,5-dimethylphenylene diamine (0.064 mole), and zinc iodide (5 mole percent) were reacted in NMP at 203° to 206° for 4 hours. The resulting brown crystals were isolated by filtration, washed with hot toluene and acetone, and dried to constant weight (yield 96.9 percent) to yield the above perinone product. The product perinone 4,5-dimethylbenzimidazole naphthimidazole naphthalene showed a strong infrared band at 1,696 cm$^{-1}$ indicative of the diimidazole structure.

EXAMPLE VII

Preparation of Unsymmetrical Perinone 4,5-Dichlorobenzimidazole Naphthimidazole Naphthalene Naphthimidazole naphthalene monoanhydride (0.0128 mole), obtained from Example I, ortho-4,5-dichlorophenylene diamine (0.064 mole), and zinc iodide (5 mole percent) were reacted in NMP at 203° to 206° for 21.5 hours. The resulting brown crystals were isolated by filtration, washed with hot toluene and acetone, and dried to constant weight (yield 89.8 percent). The product resulting 4,5-Dichlorobenzimidazole naphthimidazole naphthalene perinone showed a strong infrared band at 1,704 cm$^{-1}$ indicative of the diimidazole structure.

EXAMPLE VIII

Preparation of Unsymmetrical Perinone N-benzyl Naphthimidazole Naphthalene Imide Naphthimidazole naphthalene monoanhydride (0.0131 mole) obtained from Example I, and benzyl amine (0.13 mole) were reacted in NMP at 200° for 3 hours. The resulting brown crystals were isolated by filtration, washed with hot toluene and acetone, and dried to constant weight (yield 89.8 percent). The above product N-benzyl naphthimidazole naphthalene imide perinone showed strong infrared bands at 1,700 cm$^{-1}$ and 1,665 cm$^{-1}$ indicative of the imidazole alkyl imide structure.

EXAMPLE IX

Preparation of Unsymmetrical Perinone N-phenethyl Naphthimidazole Naphthalene Imide Naphthimidazole naphthalene monoanhydride (0.01 mole), obtained from Example II, and zinc iodide (10 mole percent) were suspended in 1-chloronaphthalene (50 milliliters) at 255°. Phenethylamine in 1-chloronaphthalene (50 milliliters) was then added dropwise by syringe pump over 4 hours. When the addition was complete, reflux was continued for another 30 minutes.

The resulting brown crystals N-phenethyl naphthimidazole naphthalene imide perinone was isolated by filtration and washed with hot toluene, and then with acetone at ambient temperature. The above product N-phenethyl naphthimidazole naphthalene imide perinone was dried to constant weight (yield 65 percent). The product showed strong infrared bands at 1,701 cm$^{-1}$ and 1,664 cm$^{-1}$ indicative of the imidazole alkyl imide structure.

EXAMPLE X

Preparation of Unsymmetrical Perinone N-(3,5-dimethylphenyl) Naphthimidazole Naphthalene Imide Naphthimidazole naphthalene monoanhydride (0.115 mole), obtained from Example II, 3,5-dimethylaniline (0.117 mole), and zinc iodide (10 mole percent) were reacted in 1-chloronaphthalene at 245° for 5.75 hours. The resulting red pigment crystals were isolated by filtration. After washing with hot toluene and acetone (at ambient temperature), the pigment was dried to constant weight (yield 86.2 percent). The product N-(3,5-dimethylphenyl) naphthimidazole naphthalene imide perinone showed strong infrared bands at 1,712 cm$^{-1}$ and 1,697 cm$^{-1}$ indicative of the imidazole phenyl imide structure. Mass spectroscopy gave a molecular ion at M/z of 493.

EXAMPLE XI

Preparation of Unsymmetrical Perinone N-(3-chlorophenyl) Naphthimidazole Naphthalene Imide Naphthimidazole naphthalene monoanhydride (0.01 mole), obtained from Example I, 3-chloroaniline (0.01 mole), and zinc iodide (10 mole percent) were reacted in 1-chloronaphthalene at 245° for 24 hours. The resulting brown crystals were isolated by filtration, washed with hot toluene and acetone, and dried to constant weight (yield 68 percent). The product N-(3-chlorophenyl) naphthimidazole naphthalene imide perinone showed strong infrared bands at 1,715 cm$^{-1}$ and 1,679 cm$^{-1}$ indicative of the imidazole phenyl imide structure. Mass spectroscopy gave a molecular ion at M/z of 499 and 501. The ratio of the isotopic cluster peaks was indicative of the incorporation of one chlorine.

EXAMPLE XII

Preparation of Unsymmetrical Perinone N-(3-fluorophenyl) Naphthimidazole Naphthalene Imide Naphthimidazole naphthalene monoanhydride (0.012 mole), obtained from Example I, 3-fluoroaniline (0.14 mole), and zinc iodide (10 mole percent) were reacted in 1-chloronaphthalene at 245° for 24 hours. The resulting red crystals were isolated by filtration, washed with toluene (90°) and acetone (25°), and dried to constant weight (yield 76 percent). The above product N-(3-fluorophenyl) naphthimidazole naphthalene imide perinone showed strong infrared bands at 1,715, 1,701 and 1,679 cm$^{-1}$ indicative of the imidazole phenyl imide structure. Mass spectroscopy gave a molecular ion at M/z of 483.

EXAMPLE XIII

Preparation of Unsymmetrical Perinone N-(2-fluorophenyl) Naphthimidazole Naphthalene Imide Naphthimidazole naphthalene monoanhydride (0.01 mole), obtained from Example I, 2-fluoroaniline (0.05 mole), and zinc iodide (10 mole percent) were reacted in 1-chloronaphthalene at 195° for 19 hours. The resulting red crystals were isolated by filtration, washed twice with toluene (90°) and once with acetone (25°), and dried to constant weight (yield 70 percent). The resulting above perinone product showed strong infrared bands at 1,715, 1,701 and 1,680 cm$^{-1}$ indicative of the imidazole phenyl imide structure. The unsymmetrical perinone products of Examples I to XIII were further purified using the small scale train sublimation apparatus described in *Journal Materials Science*, 17, 2781 (1982), the disclosure of which is totally incorporated herein by reference. Samples, 1 to 5 grams, of each perinone product, respectively, were placed at the hot segment of a glass tube (1,200 millimeters in length ×40 millimeters), and nitrogen gas at a pressure of 1 millibar was allowed to pass over the sample toward the cold end. The glass tube was placed in a steel tube which was heated at one end and cooled at the other so that a temperature gradient of 200° to 400° C. formed along the length of the tube. The sublimate crystallized within a temperature zone which depended on the volatility of the pigment. Each of the perinones was further purified by repeating this procedure. When purification was accomplished in this manner, volatile impurities were separated from the pigment perinone product and collected at the cold end of the sublimation tube. The appearance of the pigment also improved in that well formed needles or plates were obtained. The infrared spectrums also showed a decrease of other weak carbonyl absorptions in the region of 1,740 to 1,700 cm$^{-1}$ indicative of further product purification.

EXAMPLE XIV

Train Sublimation of Unsymmetrical Perinone N-Phenyl Naphthimidazole Naphthalene Monoimide:

Sublimation of a 3.7 gram sample of the N-phenyl naphthimidazole naphthalene perinone product of Example II was accomplished by repeating the above train sublimination at 1 millibar using a hot zone temperature of 490° afforded a brown purple sublimed material as shiny brown-black crystals. The resulting perinone product condensed at a temperature of between 450° and 380° C.

EXAMPLE XV

Train Sublimation of Unsymmetrical Perinone Benzimidazole Naphthimidazole Naphthalene Sublimation of a 4.8 gram sample of the benzimidazole naphthimidazole naphthalene isomers of Example II was accomplished by repeating the above train sublimination at 1 millibar using a hot zone temperature of 506° afforded a brown purple sublimed material as shiny brown-black crystals. This resulting perinone product condensed at a temperature of between 470° and 325° C.

EXAMPLE XVI

Photoconductive imaging members were prepared by providing for each separate member a titanized Mylar substrate of 75 microns in thickness with a silane layer prepared from N-methyl-3-aminopropyl trimethoxysilane, available from PCR Research Chemicals Florida, in ethanol in a 1:20 volume ratio. This layer was then dried for 5 minutes at room temperature, followed by curing at 110° C. in a forced air oven. The final silane layer was approximaely 0.1 micron in thickness. A polyester, 49,000 available from Goodyear Chemical, was then deposited in a thickness of 0.1 micron over the aforementioned layer. Deposition of the perinone photogenerator layer was accomplished thereover with a Balzers vacuum coater. The unsymmetrical perinone pigments selected were those as obtained from Examples III to XIII, respectively. The photogenerating layer had a final thickness of 0.4 micron. More specifically, the photogenerator components (1) were evaporated from an electrically heated tantalum boat and the vacuum coater was evacuated to a pressure of $10^{-5}$ Tor; each of the photogenerator layers were deposited at a rate of 1 to 4 Angstroms/second on the adhesive layer; or (2) by the solution coating of 80 weight percent of the perinone in the resin binder Makrolon, 20 weight percent, as indicated in the Table that follows.

Thereafter, the above photogenerator layers present in the respective imaging members were each overcoated with an amine charge transport layer prepared as follows. A transport layer mixture with 65 percent by weight of Makrolon, a polycarbonate resin, was mixed with 35 percent by weight of N,N'-diphenyl-N,N'-bis(3-methyl-phenyl)-1,1'-biphenyl-4,4'-diamine, and 13.5 percent by weight of methylene chloride in an amber bottle. The resulting mixture was then coated onto the above photogenerator layers using a multiple clearance film applicator (10 mils gap). The resulting members were then dried at 135° C. for 20 minutes. The transport layer thus obtained had a thickness of 20 microns.

The xerographic electrical properties of the aforementioned imaging members were then determined by electrostatically charging the surfaces thereof with a corona discharge source until the surface potential, as measured by a capacitively coupled probe attached to an electrometer, attained an initial value $V_o$ of about $-800$ volts. After resting for 0.5 second in the dark, the charged members reached a surface potential of $V_{ddp}$, dark development potential, and each member was then exposed to light from a filtered Xenon lamp with a XBO 150 watt bulb. A reduction in surface potential to a $V_{bg}$ value, background potential, due to photodischarge effect was observed. The dark decay in volt/second was calculated as $(V_o - V_{ddp})/0.5$. The percent of photodischarge was calculated as 100 percent $(V_{ddp} - V_{bg})/V_{ddp}$. The desired wavelength and energy of the expose light was determined by the type of filters placed in front of the lamp. The broad band white light (400 to 700 nanometers) photosensitivity of these imaging members were measured by using an infrared cut-off filter whereas the monochromatic light photosensitivity was determined using narrow band-pass filter.

The photosensitivity of the imaging members is usually provided in terms of the amount of expose energy in erg/cm$^2$, designated as $E_{\frac{1}{2}}$, required to achieve 50 percent of photodischarge from the dark development potential. The higher the photosensitivity, the smaller is the $E_{\frac{1}{2}}$ value.

Table 1 summarizes the xerographic electricals of some of the aforementioned imaging members or devices. The dark decay and white light photosensitivity values are listed. These devices exhibit excellent sensitivity and very low dark decay.

TABLE 1

| Imaging Member | Perinone Photogenerator | Type of Generator Layer | Dark Decay V/s | $\lambda = 550$ nm $E_{\frac{1}{2}}$ erg/cm$^2$ |
|---|---|---|---|---|
| 1 | Perinone of Example III | Vacuum coated | 7 | 17.7 |
| 2 | Perinone of Example III | Binder dispersion | 22 | 8.0 |
| 3 | Perinone of Example IV | Vacuum coated | 4 | 31.0 |
| 4 | Perinone of Example IV | Binder dispersion | 17 | 17.4 |
| 5 | Perinone of Example V | Vacuum coated | 6 | 4.7 |
| 6 | Perinone of Example V | Binder dispersion | 17 | 3.5 |
| 7 | Perinone of Example VI | Vacuum coated | 4 | 2.8 |
| 8 | Perinone of Example VI | Binder dispersion | 16 | 3.9 |
| 9 | Perinone of Example VII | Vacuum coated | 9 | 4.0 |
| 10 | Perinone of Example VII | Binder dispersion | 46 | 3.2 |

The titanium Mylar/silane/polyester 49,000 layer can be of a thickness of from about 0.05 to 1.0 micron in an embodiment of the poresent invention, and the hole transport amine layer (35 weight percent) can be of a thickness of 20 microns.

Other modifications of the present invention may occur to those skilled in the art subsequent to a review of the present application. These modifications, including equivalents thereof, are intended to be included within the scope of the present invention. Thus, for example, the transport layers of U.S. Pat. No. 4,921,773, the disclosure of which is totally incorporated herein by reference, can be selected for the imaging members of the present invention.

Figure 1B:
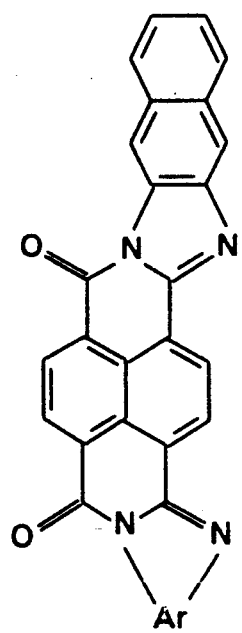
Figure 1C:
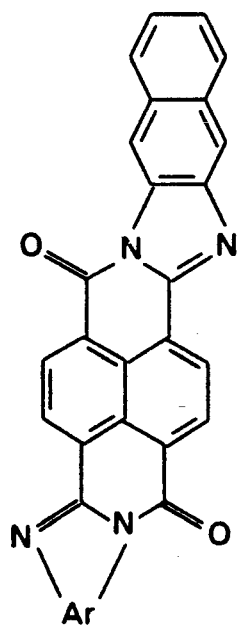

What is claimed is:

1. A photoconductive imaging member consisting essentially of a supporting substrate, a photogenerating layer comprised of the unsymmetrical perinone as represented by the formula of FIGS. 1B, 1C, or mixtures thereof wherein Ar is an aromatic diamine, a heterocyclic diamine, or an aliphatic diamine, and a charge transport layer.

2. An imaging member in accordance with claim 1 wherein Ar is orthophenylene diamine, diamino pyrazine, or alkylene diamine.

3. An imaging member in accordance with claim 1 wherein the unsymmetrical perinone is N-phenyl 2', 3'-naphthimidazole naphthalene perinone monoimide; N-benzyl 2',3'-naphthimidazole naphthalene perinone monoimide; N-phenethyl 2', 3'-naphthimidazole naphthalene perinone monoimide; N-3-chlorophenyl 2', 3'-naphthimidazole naphthalene perinone monoimide; N-3-fluorophenyl 2', 3'-naphthimidazole naphthalene perinone monoimide; N-2-fluorophenyl 2', 3'-naphthimidazole naphthalene perinone monoimide; N-pentafluorophenyl 2', 3'-naphthimidazole naphthalene perinone monoimide; cis and trans benzimidazole 2', 3'-naphthimidazole perinone; cis and trans 2,3-dichlorobenzimidazole 2', 3'-naphthimidazole perinone and 2,3-dimethylbenzimidazole 2', 3'-naphthimidazole perinone; and cis and trans imidazole 2', 3'-naphthimidazole perinone.

4. A method of imaging or printing which comprises generating an image on the imaging member of claim 1; developing the image generated; transferring the developed image to a suitable substrate; and affixing the image thereto.

* * * * *